(12) United States Patent
Cumming

(10) Patent No.: US 9,655,716 B2
(45) Date of Patent: May 23, 2017

(54) SEMI-RIGID FRAMEWORK FOR A PLATE HAPTIC ACCOMMODATING INTRAOCULAR LENS

(71) Applicant: James Stuart Cumming, Laguna Beach, CA (US)

(72) Inventor: James Stuart Cumming, Laguna Beach, CA (US)

(*) Notice: Subject to any disclaimer, the term of this patent is extended or adjusted under 35 U.S.C. 154(b) by 0 days.

(21) Appl. No.: 14/968,518

(22) Filed: Dec. 14, 2015

(65) Prior Publication Data

US 2016/0199175 A1 Jul. 14, 2016

Related U.S. Application Data

(63) Continuation of application No. 14/270,166, filed on May 5, 2014, now Pat. No. 9,211,186, which is a continuation of application No. 13/155,327, filed on Jun. 7, 2011, now Pat. No. 8,764,823.

(60) Provisional application No. 61/398,107, filed on Jun. 21, 2010, provisional application No. 61/398,098, filed on Jun. 21, 2010, provisional application No. 61/398,115, filed on Jun. 21, 2010, provisional application No. 61/398,099, filed on Jun. 21, 2010.

(51) Int. Cl.
*A61F 2/16* (2006.01)

(52) U.S. Cl.
CPC ............ *A61F 2/16* (2013.01); *A61F 2/1624* (2013.01); *A61F 2/1629* (2013.01); *A61F 2002/169* (2015.04); *A61F 2002/1681* (2013.01); *A61F 2002/1682* (2015.04); *A61F 2002/1689* (2013.01); *A61F 2002/16905* (2015.04); *A61F 2230/0006* (2013.01); *A61F 2230/0069* (2013.01)

(58) Field of Classification Search
CPC ................ A61F 2/16; A61F 2002/1681; A61F 2002/1689
See application file for complete search history.

(56) References Cited

U.S. PATENT DOCUMENTS

| 2,834,023 A | 5/1958 | Lieb |
| 4,073,014 A | 2/1978 | Poler |
| 4,118,808 A | 10/1978 | Poler |

(Continued)

FOREIGN PATENT DOCUMENTS

| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troubleshooting, 2003, p. 81.

(Continued)

*Primary Examiner* — David H Willse
*Assistant Examiner* — Tiffany Shipmon
(74) *Attorney, Agent, or Firm* — Sheppard, Mullin Richter & Hampton LLP

(57) ABSTRACT

A plate haptic for an accommodating intraocular lens. The plate haptic has a haptic body that is substantially rigid in a longitudinal direction and substantially flexible in a transverse direction. A chassis is integral to the haptic body. The chassis causes the haptic body to be substantially more rigid in a longitudinal direction than in a transverse direction.

45 Claims, 10 Drawing Sheets

(56) References Cited

U.S. PATENT DOCUMENTS

| | | | |
|---|---|---|---|
| 4,122,556 | A | 10/1978 | Poler |
| 4,159,546 | A | 7/1979 | Shearing |
| 4,168,547 | A | 9/1979 | Konstantinov et al. |
| 4,173,798 | A | 11/1979 | Welsh |
| 4,174,543 | A | 11/1979 | Kelman |
| 4,206,518 | A | 6/1980 | Jardon et al. |
| 4,244,060 | A | 1/1981 | Hoffer |
| 4,254,509 | A | 3/1981 | Tennant |
| 4,277,851 | A | 7/1981 | Choyce et al. |
| 4,298,995 | A | 11/1981 | Poler |
| 4,304,012 | A | 12/1981 | Richard |
| 4,409,690 | A | 10/1983 | Gess |
| 4,409,691 | A | 10/1983 | Levy |
| 4,424,597 | A | 1/1984 | Schlegel |
| 4,441,217 | A | 4/1984 | Cozean, Jr. |
| 4,477,931 | A | 10/1984 | Kelman |
| 4,573,998 | A | 3/1986 | Mazzocco |
| 4,585,457 | A | 4/1986 | Kalb |
| 4,605,411 | A | 8/1986 | Fedorov et al. |
| 4,629,462 | A | 12/1986 | Feaster |
| 4,648,878 | A | 3/1987 | Kelman |
| 4,664,665 | A | 5/1987 | Reuss et al. |
| 4,664,666 | A | 5/1987 | Barrett |
| 4,673,406 | A | 6/1987 | Schlegel |
| 4,681,102 | A | 7/1987 | Bartell |
| 4,704,123 | A | 11/1987 | Smith |
| 4,710,195 | A | 12/1987 | Glovinazzo |
| 4,718,904 | A | 1/1988 | Thornton |
| 4,737,322 | A | 4/1988 | Bruns et al. |
| 4,738,680 | A | 4/1988 | Herman |
| 4,743,254 | A | 5/1988 | Davenport |
| 4,753,655 | A | 6/1988 | Hecht |
| 4,759,761 | A | 7/1988 | Portnoy |
| 4,763,650 | A | 8/1988 | Hauser |
| 4,765,329 | A | 8/1988 | Cumming et al. |
| 4,769,033 | A | 9/1988 | Nordan |
| 4,769,035 | A | 9/1988 | Kelman |
| 4,772,283 | A | 9/1988 | White |
| 4,778,463 | A | 10/1988 | Hetland |
| 4,781,719 | A | 11/1988 | Kelman |
| 4,790,847 | A | 12/1988 | Woods |
| 4,793,344 | A | 12/1988 | Cumming et al. |
| 4,813,955 | A | 3/1989 | Achatz et al. |
| 4,816,030 | A | 3/1989 | Robinson |
| 4,840,627 | A | 6/1989 | Blumenthal |
| 4,842,599 | A | 6/1989 | Bronstein |
| 4,842,601 | A | 6/1989 | Smith |
| 4,846,833 | A | 7/1989 | Cumming |
| 4,862,885 | A | 9/1989 | Cumming |
| 4,865,601 | A | 9/1989 | Caldwell et al. |
| 4,868,251 | A | 9/1989 | Reich et al. |
| 4,880,427 | A | 11/1989 | Anis |
| 4,888,012 | A | 12/1989 | Horn et al. |
| 4,892,543 | A | 1/1990 | Turley |
| 4,919,130 | A | 4/1990 | Stoy et al. |
| 4,932,966 | A | 6/1990 | Christie et al. |
| 4,932,968 | A | 6/1990 | Caldwell et al. |
| 4,932,970 | A | 6/1990 | Portney |
| 4,936,850 | A | 6/1990 | Barrett |
| 4,963,148 | A | 10/1990 | Sulc et al. |
| 4,969,897 | A | 11/1990 | Kalb |
| 4,976,716 | A | 12/1990 | Cumming |
| 4,978,354 | A | 12/1990 | Van Gent |
| 4,994,082 | A | 2/1991 | Richards et al. |
| 5,047,051 | A | 9/1991 | Cumming |
| 5,066,297 | A | 11/1991 | Cumming |
| 5,074,876 | A * | 12/1991 | Kelman .......... A61F 2/1616 623/6.17 |
| 5,078,742 | A | 1/1992 | Dahan |
| 5,139,518 | A | 8/1992 | White |
| 5,141,507 | A | 8/1992 | Paraekh |
| 5,152,788 | A | 10/1992 | Isaacson et al. |
| 5,152,789 | A | 10/1992 | Willis |
| 5,171,319 | A | 12/1992 | Keates et al. |
| 5,171,320 | A | 12/1992 | Nishi |
| 5,180,390 | A | 1/1993 | Drews |
| 5,217,490 | A | 6/1993 | Sayano et al. |
| 5,275,604 | A | 1/1994 | Rheinish et al. |
| 5,275,623 | A | 1/1994 | Sarfarazi |
| 5,275,624 | A | 1/1994 | Hara et al. |
| 5,290,310 | A | 3/1994 | Makower et al. |
| 5,304,182 | A | 4/1994 | Rheinish et al. |
| 5,324,306 | A | 6/1994 | Makower et al. |
| 5,326,347 | A | 7/1994 | Cumming |
| 5,366,502 | A | 11/1994 | Patel |
| 5,376,115 | A | 12/1994 | Jansen |
| 5,425,734 | A | 6/1995 | Blake |
| 5,443,506 | A | 8/1995 | Garabet |
| 5,474,562 | A | 12/1995 | Orchowski et al. |
| 5,476,514 | A | 12/1995 | Cumming |
| 5,489,302 | A | 2/1996 | Skottun |
| 5,496,366 | A | 3/1996 | Cumming |
| 5,522,891 | A | 6/1996 | Klaas |
| 5,562,731 | A | 10/1996 | Cumming |
| 5,578,042 | A | 11/1996 | Cumming |
| 5,578,078 | A | 11/1996 | Nakajima et al. |
| 5,607,472 | A | 3/1997 | Thompson |
| 5,611,968 | A | 3/1997 | Grisoni et al. |
| 5,647,865 | A | 7/1997 | Swinger |
| 5,674,282 | A | 10/1997 | Cumming |
| 5,686,414 | A | 11/1997 | Scannon |
| 5,699,142 | A | 12/1997 | Lee et al. |
| 5,716,403 | A | 2/1998 | Tran et al. |
| 5,800,532 | A | 9/1998 | Lieberman |
| 5,837,156 | A | 11/1998 | Cumming |
| 5,843,187 | A | 12/1998 | Bayers |
| 5,873,879 | A | 2/1999 | Figueroa et al. |
| 5,919,230 | A | 7/1999 | Sambursky |
| 5,944,725 | A | 8/1999 | Cicenas et al. |
| 5,968,094 | A | 10/1999 | Werblin et al. |
| 5,984,914 | A | 11/1999 | Cumming |
| 6,007,579 | A | 12/1999 | Lipshitz et al. |
| 6,013,101 | A | 1/2000 | Israel |
| 6,015,435 | A | 1/2000 | Valunin et al. |
| 6,027,531 | A | 2/2000 | Tassignon |
| 6,051,024 | A | 4/2000 | Cumming |
| 6,066,171 | A | 5/2000 | Lipshitz et al. |
| 6,066,172 | A | 5/2000 | Huo et al. |
| 6,113,633 | A | 9/2000 | Portney |
| 6,129,760 | A | 10/2000 | Fedorov et al. |
| 6,161,544 | A | 12/2000 | DeVore |
| 6,164,282 | A | 12/2000 | Gwon et al. |
| 6,176,878 | B1 | 1/2001 | Gwon et al. |
| 6,179,870 | B1 | 1/2001 | Sourdille et al. |
| 6,193,750 | B1 | 2/2001 | Cumming |
| 6,197,058 | B1 | 3/2001 | Portney |
| 6,197,059 | B1 | 3/2001 | Cumming |
| 6,217,612 | B1 | 4/2001 | Woods |
| 6,299,641 | B1 | 10/2001 | Woods |
| 6,302,911 | B1 | 10/2001 | Hanna |
| 6,322,589 | B1 | 11/2001 | Cumming |
| 6,342,073 | B1 | 1/2002 | Cumming et al. |
| 6,387,126 | B1 | 5/2002 | Cumming |
| 6,391,056 | B2 | 5/2002 | Cumming |
| 6,406,494 | B1 | 6/2002 | Laguette et al. |
| 6,409,763 | B1 | 6/2002 | Brady |
| 6,413,276 | B1 | 7/2002 | Werblin |
| 6,419,697 | B1 | 7/2002 | Kelman |
| 6,423,094 | B1 | 7/2002 | Sarfarazi |
| 6,443,985 | B1 | 9/2002 | Woods |
| 6,451,056 | B1 * | 9/2002 | Cumming .......... A61F 2/1629 623/6.18 |
| 6,461,384 | B1 | 10/2002 | Hoffmann et al. |
| 6,488,708 | B2 | 12/2002 | Sarfarazi |
| 6,494,911 | B2 | 12/2002 | Cumming |
| 6,497,708 | B1 | 12/2002 | Cumming |
| 6,503,275 | B1 | 1/2003 | Cumming |
| 6,503,276 | B2 | 1/2003 | Lang et al. |
| 6,517,577 | B1 | 2/2003 | Callahan et al. |
| 6,524,340 | B2 | 2/2003 | Israel |
| 6,540,353 | B1 | 4/2003 | Dunn |
| 6,558,420 | B2 | 5/2003 | Green |
| 6,613,343 | B2 | 9/2003 | Dillingham et al. |
| 6,616,691 | B1 | 9/2003 | Tran |

(56) References Cited

U.S. PATENT DOCUMENTS

| | | |
|---|---|---|
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 * | 2/2005 | Cumming ............. A61F 2/1629 623/6.18 |
| 6,858,040 B2 | 2/2005 | Nguyen et al. |
| 6,881,225 B2 | 4/2005 | Okada |
| 6,884,263 B2 | 4/2005 | Valyunin |
| 6,921,416 B2 | 7/2005 | Khoury |
| 6,926,736 B2 | 8/2005 | Peng |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,388,608 B1 | 3/2013 | Kaluzna |
| 8,523,942 B2 | 9/2013 | Cumming |
| 8,734,512 B2 | 5/2014 | Cumming |
| 8,764,823 B2 | 7/2014 | Cumming |
| 9,034,036 B2 | 5/2015 | Cumming |
| 2001/0001836 A1 * | 5/2001 | Cumming ............. A61F 2/1629 623/6.37 |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0215207 A1 | 10/2004 | Cumming |
| 2004/0220666 A1 | 11/2004 | Cumming |
| 2004/0243232 A1 | 12/2004 | Cumming |
| 2004/0249456 A1 | 12/2004 | Cumming |
| 2005/0021140 A1 | 1/2005 | Liao |
| 2005/0027354 A1 | 2/2005 | Brady et al. |
| 2005/0075732 A1 | 4/2005 | Israel |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 | 5/2006 | Blake et al. |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0032867 A1 | 2/2007 | Cumming |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming et al. |
| 2007/0244472 A1 | 10/2007 | Kuhn et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2009/0234449 A1 | 9/2009 | De Juan, Jr. et al. |
| 2009/0248154 A1 | 10/2009 | Dell |
| 2010/0004742 A1 | 1/2010 | Cumming |
| 2010/0057202 A1 | 3/2010 | Bogaert |
| 2011/0313519 A1 | 12/2011 | Cumming |
| 2011/0313524 A1 | 12/2011 | Cumming |
| 2011/0313525 A1 | 12/2011 | Cumming |
| 2011/0313526 A1 | 12/2011 | Cumming |
| 2012/0296424 A1 | 11/2012 | Betser |
| 2012/0310344 A1 | 12/2012 | Cumming |
| 2013/0073039 A1 | 3/2013 | Mirlay |
| 2013/0231742 A1 | 9/2013 | Deacon et al. |
| 2014/0088699 A1 | 3/2014 | Cumming |
| 2014/0094909 A1 | 4/2014 | Cumming |
| 2014/0155871 A1 | 6/2014 | Cumming |
| 2015/0073550 A1 | 3/2015 | Cumming |
| 2015/0088254 A1 | 3/2015 | Cumming |
| 2015/0182327 A1 | 7/2015 | Cumming |
| 2015/0182328 A1 | 7/2015 | Cumming |

FOREIGN PATENT DOCUMENTS

| | | |
|---|---|---|
| DE | 3626869 | 2/1988 |
| FR | 2728459 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | WO 2009/048656 | 4/2009 |
| WO | WO 2009/086511 | 7/2009 |

OTHER PUBLICATIONS

International Search Report and Written Opinion for PCT/US13/61452 dated Feb. 24, 2014 in 11 pages.

(56) References Cited

OTHER PUBLICATIONS

International Search Report and Written Opinion for PCT/US2014/057037 dated Jan. 20, 2015 in 12 pages.
International Search Report and Written Opinion for PCT/US2014/072518 dated Jul. 23, 2015 in 15 pages.

* cited by examiner

SEMI-RIGID FRAMEWORK FOR A PLATE HAPTIC ACCOMMODATING INTRAOCULAR LENS

CROSS-REFERENCE TO RELATED APPLICATIONS

This application is a continuation of U.S. patent application Ser. No. 14/270,166, filed May 5, 2014, which is a continuation of U.S. patent application Ser. No. 13/155,327, now U.S. Pat. No. 8,764,823, filed Jun. 7, 2011, which claims the benefit of the filing of U.S. Provisional Patent Application No. 61/398,107 filed Jun. 21, 2010; U.S. Provisional Patent Application No. 61/398,098 filed Jun. 21, 2010; U.S. Provisional Patent Application No. 61/398,115, filed Jun. 21, 2010; and U.S. Provisional Patent Application No. 61/398,099, filed Jun. 21, 2010, the contents and disclosure of which are fully incorporated herein by reference.

This application is related to U.S. Non-Provisional patent application Ser. No. 13/017,189, filed Feb. 14, 2011; and U.S. Non-Provisional patent application Ser. No. 13/092, 359, filed Apr. 22, 2011; and U.S. Non-Provisional patent application Ser. No. 13/111,599, filed May 19, 2011, the contents and disclosure of which are fully incorporated herein by reference.

BACKGROUND OF THE INVENTION

Accommodating Intraocular Lenses were developed in the early 1900's and have been sold in Europe for the last ten years and later in the U.S. They function by means of forward movement of the optic upon constriction of the ciliary muscle which increases the pressure in the posterior part of the eye with a simultaneous decrease in pressure in the front part of the eye pressure. The reverse pressure changes take place upon relaxation of the ciliary muscle, which results in the backwards movement of the lens for distance vision. The forward movement of the lens optic enables the patient implanted with the lens to automatically change their vision from distance to see at intermediate and near.

The currently marketed accommodating plate haptic intraocular lenses provide excellent distance and intermediate vision but sometimes require weak, +1.00, reading glasses for prolonged reading, for seeing small print, or reading in dim lighting conditions. The embodiments relating to the present invention presented herein are designed to substantially reduce the need for any reading glasses.

It is important for intraocular lenses to have a consistent location along the axis of the eye to provide good uncorrected distance vision and to center in the middle of the vertical meridian of the eye. Without excellent uncorrected distance vision there is no point in implanting an accommodating lens whose function is to enable patients to be without glasses.

The word "haptic" has been used to describe an attachment to intraocular lenses. The original intraocular lens consisted of a single optic. These single optic lenses, without any attachments, were first implanted in London by Harold Ridley in 1949. These lenses frequently de-centered and it was discovered that there was a need to center and fixate the lens optic in the vertical meridian of the eye. The first attachments to the optic were called "haptics". They consisted of multiple flexible loops of various designs, J loops, C loops, closed loops and flexible radial arms. Later, these loops which became commonly referred to as "haptics" were replaced in some lens designs with plates, called "plate haptics". Current plate haptic designs reduces the incidence of post-operative complications of cataract surgery, including retinal detachment and cystoid macular edema. Also, because of the more consistent location of the lens along the axis of the eye, the uncorrected post-operative visual acuities are superior to those of loop haptics.

During constriction of the circular ciliary muscle in an eye fitted with a plate haptic accommodating intraocular lens, the diameter of the ciliary muscle decreases and the muscle compresses the distal ends of the plate haptics, moving them centrally. Because uni-planar plate haptics tend to vault posteriorly when placed into the capsular bag, the central movement of the plate haptics causes their proximal end attached to the optic to move posteriorly and centrally. This posterior movement of the plates increases the vitreous cavity pressure behind the lens and its optic and simultaneously decreases the vitreous cavity pressure in the anterior chamber of the eye-and accommodates for near vision.

The current accommodating intraocular lenses utilize an oblong lens body design having flexible plate haptics connected to the lens optics by a single transverse hinge across the plate haptic. This promotes accommodation by allowing the optic to move forwards and backwards relative to the outer, or distal, ends of the plates. Such accommodating lenses are found in U.S. Pat. Nos. 5,476,514 and 5,496,366, both to Cumming, the disclosures of which are herein incorporated by reference. However, such designs do not permit adequate movement of the optic to a change in vitreous cavity pressure to allow many patients to read comfortably at near without glasses.

Current plate haptics are constructed of silicone, hydrogel or acrylic and are generally flexible. Due to this flexibility, current plate haptics tend to slightly buckle or deform when longitudinally compressed by the constriction of the ciliary muscle. This buckling reduces the possible pressure applicable by the plates on the vitreous cavity with constriction of the ciliary muscle.

Furthermore, when the accommodating lens plate haptic is fibrosed into the capsular bag of an eye after cataract surgery, sometimes several weeks or months following the surgery, a complication can occur. The lens can deform to a "Z" dislocated shape. This occurs when there is little sandwiching of the distal tip of the plate haptics between the remaining anterior and the posterior walls of the capsular bag.

SUMMARY OF THE INVENTION

A plate haptic accommodating intraocular lens design according to an embodiment of the present invention is described that overcomes the deficiencies of present designs noted above.

A flat, longitudinal accommodating intraocular lens is provided, having distinct separate plate haptics that are rigid longitudinally, but flexible transversely, and that extend to partially surround the optic. The transverse flexibility of the plate haptics permits the accommodating intraocular lens to be folded longitudinally and inserted into the eye via a small incision therein. The longitudinal rigidity of the plate haptics inhibits the buckling or deforming of the plate haptic during accommodation. Thus, the plate haptics may exert more pressure on the vitreous cavity, thereby increasing the forward movement of the lens optic.

The flat plate haptics may have a groove or hinge portion across the width of its proximal ends adjacent to the optic. This hinge may be weakened by comprising at least two separate spaced apart narrow hinges on each edge of the plate haptics, thereby, reducing the overall length of the hinge. This plural strap design stabilizes the lens optic while reducing the resistance of the optic to a change in vitreous cavity pressure, thereby, allowing more movement of the optic along the axis of the eye. Further stabilization is achieved by making the haptics as wide, or wider, than the optic and extending the lateral proximal ends of the plate haptics to partially surround the optic. The plate haptics may be made rigid longitudinally by incorporating into the length of the haptics a rigid frame structure.

Thus, an accommodating lens according to the present invention may stabilize the solid, single, flexible lens optic, prevent tilt, provide more movement of the optic for better near vision and center and fixate the lens in the capsular bag with finger-like flexible loops at the distal ends of the plates. This accommodating lens improves near vision by reducing the resistance to pressure changes on the optic with contraction and relaxation of the ciliary muscle and by further increasing the vitreous cavity pressure by means of the lateral plate haptic extensions, which with accommodation and constriction of the ciliary muscle are forced posteriorly such that their proximal ends to then lie posterior to the optic.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE DRAWINGS

Illustrated in the accompanying drawing(s) is at least one of the best mode embodiments of the present invention. In such drawing(s).

DETAILED DESCRIPTION OF THE PREFERRED EMBODIMENT

The above described drawing figures illustrate the described invention and method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

Figure 1:
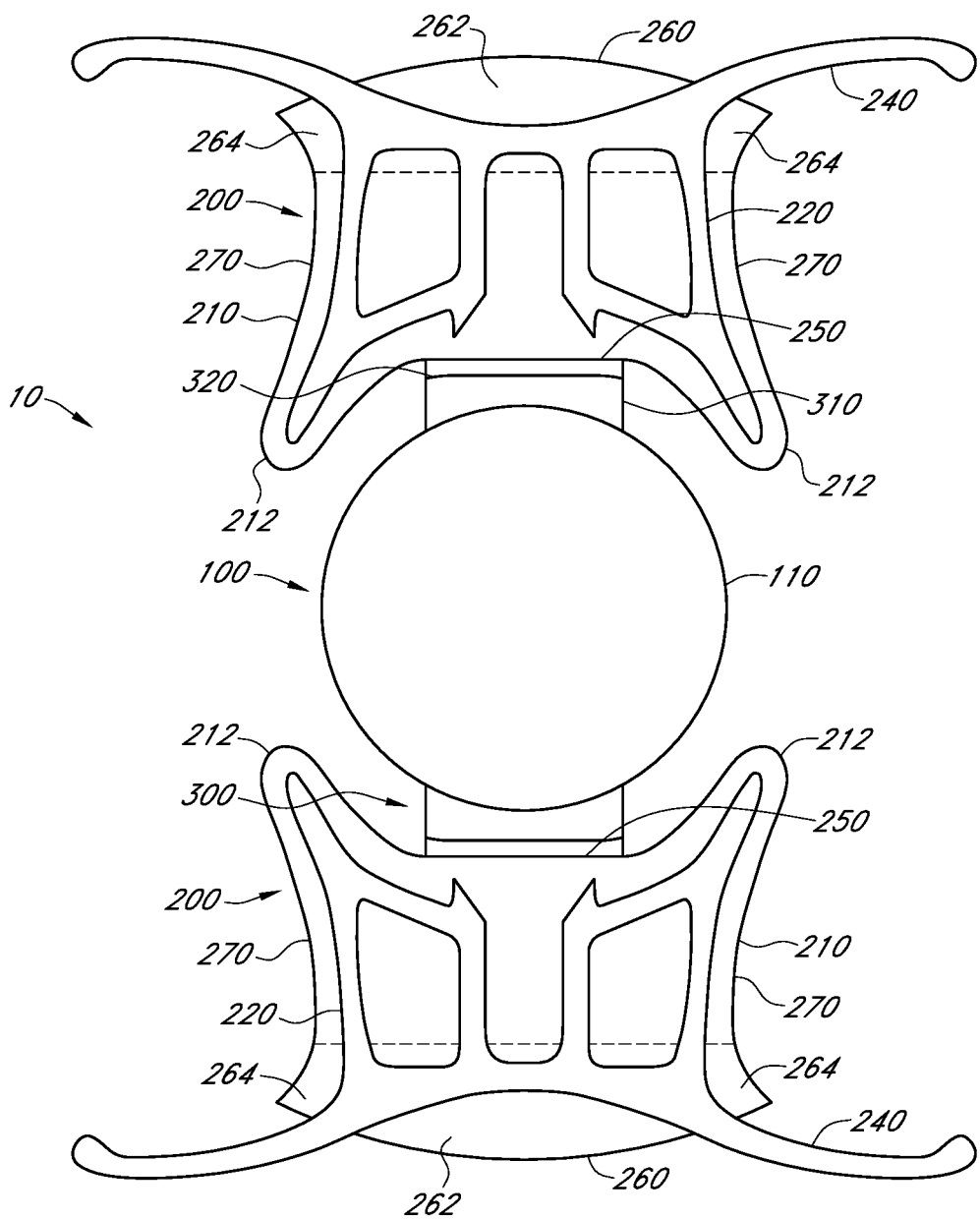
FIGS. 1-2 illustrate top views of a semi-rigid framework for a plate haptic accommodating intraocular lens according to an embodiment of the present invention.

FIG. 1 illustrates an accommodating intraocular lens 10. The accommodating intraocular lens 10 comprises: a plurality of plate haptics 200 disposed on opposing ends of a lens optic 100. The plate haptics 200 are flexibly coupled to the lens optic 100 at a hinge portion 300.

Each plate haptic 200 comprises: a haptic body 210; a chassis 220 integral to the haptic body 210; a centration member 240; a proximal portion 250; a distal portion 260; and opposing lateral portions 270. In some embodiments, the width of the plate haptic 200 may be between 4.0 and 6.0 mm, and the thickness of the plate haptic may be between 0.15 and 0.75 mm.

The chassis 220 is integral to the haptic body 210 and may be substantially more rigid in a longitudinal direction than in a transverse direction and may cause the plate haptic 200 to be substantially rigid in a longitudinal direction and substantially flexible in a transverse direction. The chassis 220 may be separate from the haptic body 210, or may be unitary therewith. In at least one embodiment, the haptic body 210 is made of a first material selected from silicone, acrylic, hydro gels, or other similar material, and the chassis 220 is made of a second material selected from polyimide, prolene, PMMA, titanium, and other similar material. In at least one other embodiment, the haptic body 210 is made of the first material and the chassis 220 is a thickened portion of the haptic body. Thus, the haptic body 210 may be substantially rigid in a longitudinal direction and substantially flexible in a transverse direction. The substantially flexible nature of the plate haptic 200 in the lateral direction permits folding the intraocular lens in the lateral direction so that it may be inserted into the eye through a small incision. However, the substantially rigid nature of the plate haptic 200 in the longitudinal direction ensures that when the ciliary muscle exerts radial pressure on the distal portion 260 during accommodation, the plate haptic 200 will move centrally and posteriorly towards the optic 100 without bending or buckling. Thus, a greater response to vitreous pressure change is achieved.

Figure 3:
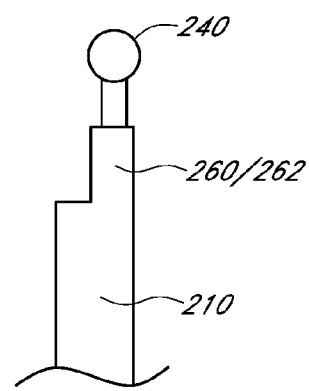
FIG. 3 illustrates a side view of a plate haptic according to an embodiment of the present invention.

The distal portion 260 of the plate haptic 200 comprises a distal flange 262 extending distally and laterally therefrom, the distal flange comprising opposing lateral appendages 264 operable to engage the capsular bag. These lateral appendages 264 may be substantially triangular in shape, but other shapes are also contemplated. As shown in FIG. 3, the distal flange is preferably thinner than the haptic body from which it extends. On insertion into the eye, the distal flange 262 increases the contact area and provides additional fixation and support for the lens within the capsular bag.

Figure 2:
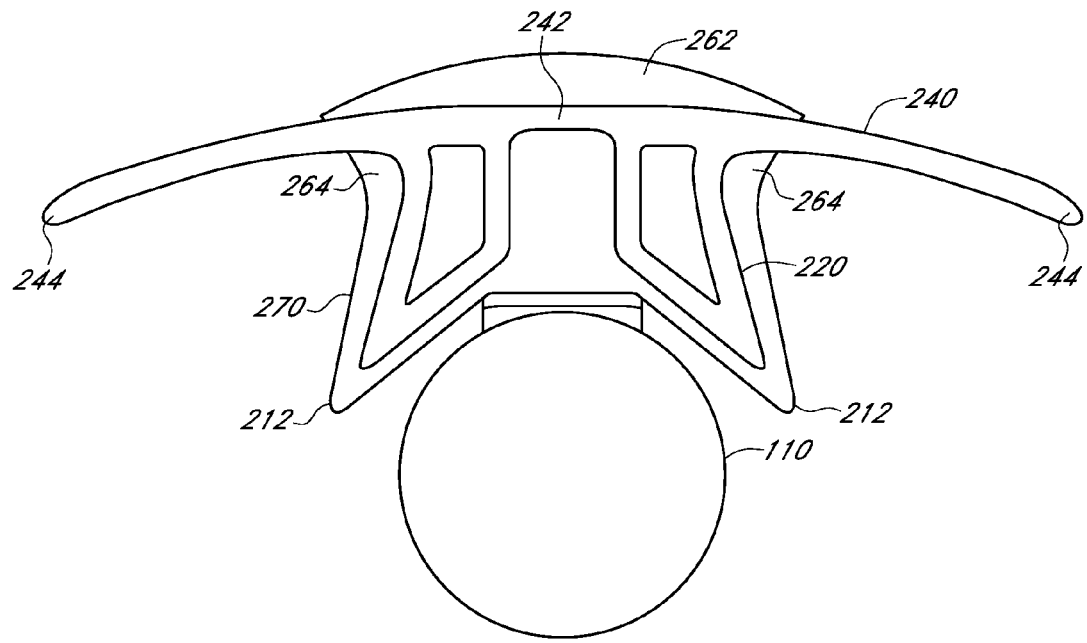
Figure 4A:
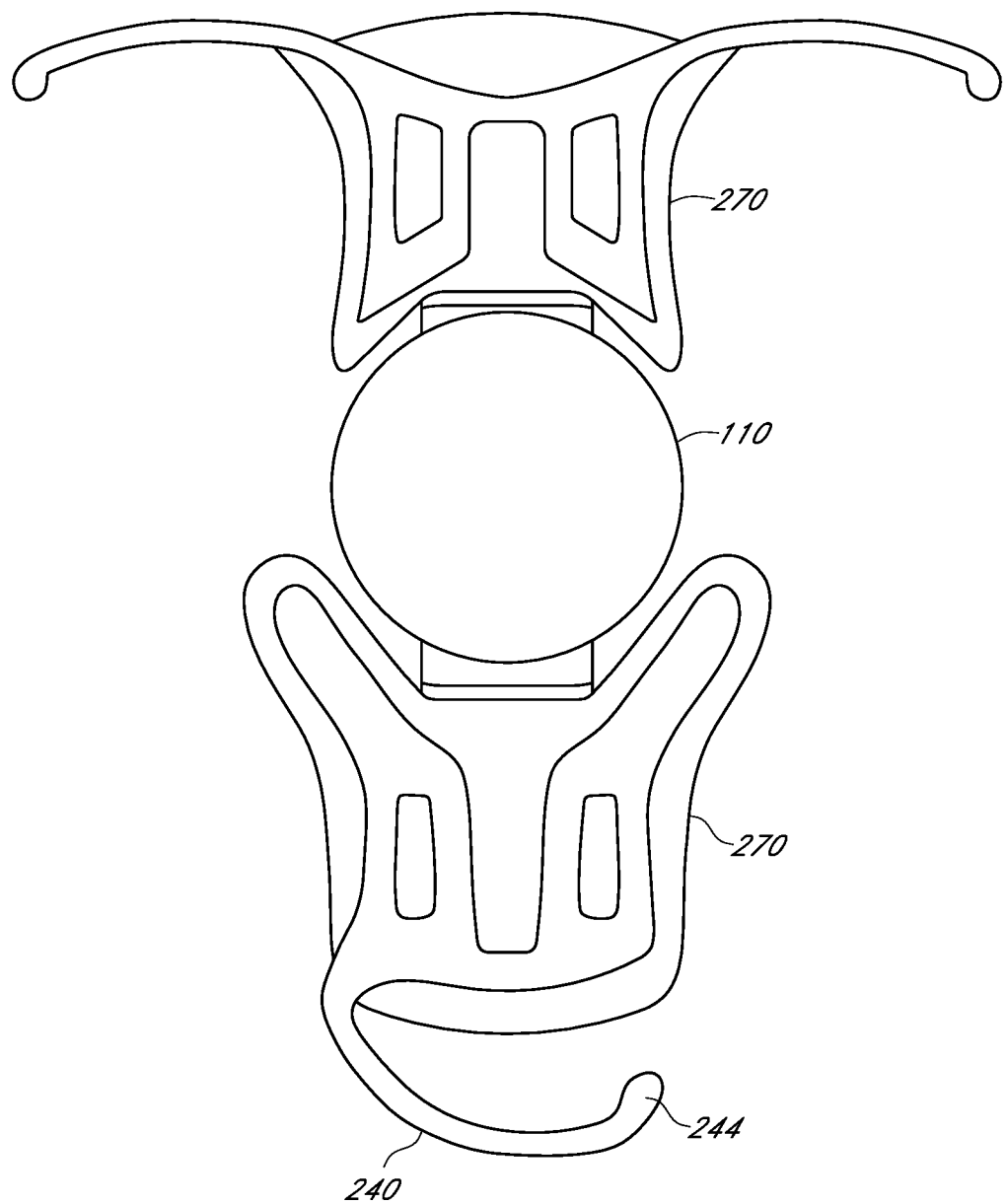
FIG. 4A-4C illustrates top views of exemplary plate haptic accommodating intraocular lens according to various embodiment of the present invention.

The centration member 240 is integral to the distal portion 260 and extends therefrom. The centration member 240 comprises: a base 242 integral to the haptic body 210 and at least one loop 244 extending from the base 242 beyond the haptic body 244 to engage a capsular bag. As shown in FIG. 2, the centration member 240 may comprise opposing loops 244 extending from the base 242 beyond the lateral sides 270 of the plate haptic 200. However, as shown in FIG. 5G, the centration member 240 may comprise a single loop 244 extending beyond the distal portion 260 at a location substantially nearer to one lateral side 270, towards the other lateral side 270. Additionally, as shown in FIG. 4A, the centration member 240 may comprise a single loop 244 extending beyond one lateral side 270 of the plate haptic 200. In at least one embodiment, the centration member 240 is integral to the chassis 220. It is important to note that each plate haptic 200 may comprise a different centration member 240, or none at all. In one embodiment, the length of the accommodating intraocular lens without the centration member 240 is 10.5 to 11.0 mm, while the length of the accommodating intraocular lens with the centration member 240 is 11.5 to 12.5 mm. The flexible loops 244 are preferably compressible centrally to fix and center the accommodating intraocular lens within the capsular while minimizing tilt.

The plate haptic 200 may further comprise a plurality of opposing tabs 212, or paddles, each tab 212, or paddle, formed by the intersection of the proximal portion 250 and an associated lateral side 270. Each tab 212 may comprise at least one of: the haptic body 210 and the chassis 220. In some embodiments, the tabs 212 are laterally divergent. As shown in FIG. 1, the tabs 212 may comprise the haptic body 210 and the chassis 220 integral thereto. However, as shown in FIG. 5B, the tabs 212 may comprises a chassis frame portion 222 extending beyond the haptic body 210. The tabs 212 preferably extend from the haptic body 210 to partially surround the optic 100 in combination with the proximal portion 250 of the haptic body 210. In at least one preferred embodiment, the tabs 212 in combination with the proximal portion 250 substantially occupy at least one-quarter of an optic periphery 110. Such wide tab construction offers increased stabilization of the optic and the plate.

The hinge portion 300 flexibly couples each plate haptic 200 to the lens optic 100. As shown in FIG. 1, at least one strap 310 connects the proximal portion 250 of the plate haptic 200 to the periphery 110 of the lens optic 100. In one embodiment, the strap 310 may be 0.5 to 4.0 mm in width. The strap 310 is preferably flexible and/or stretchable or elastic such that it may respond to an increase in vitreous pressure changes that may cause central and posterior movement of the plate haptics 200, thus permitting the optic 100 to move forward along the axis of the eye. The strap may comprise a first surface and a second surface in opposition thereto. The strap may further comprise at least one groove 320 traversing at least one of the first or second surfaces. The groove 320 preferably traverses the strap 310 parallel or tangential to at least one of the proximal portion 250 or the optic periphery 110. The groove 320 further weakens the straps 310 resistance to vitreous pressure changes and permits greater accommodation. As shown in FIG. 5G, the hinge portion 300 may comprise at least two straps 310 that are laterally spaced apart from each other, equidistant from a longitudinal axis of the intraocular lens, such that the separation of straps 310 ensures the transferred pressure is uniform. The hinge portion 300 may have a thickness that is half the thickness of the plate haptic 200, or preferably a thickness of 0.10 to 0.30 mm. Preferably, the strap 310 is approximately 1 to 1.5 mm long and may be thinner than the haptic body 210.

FIG. 5 illustrates the chassis 220 according to various embodiments. The chassis 220 may comprise a plurality of integral frame members 222 that are spaced apart from each other so as to form a plurality of apertures 224 therebetween, the apertures comprising the haptic body 210.

Figure 5A:
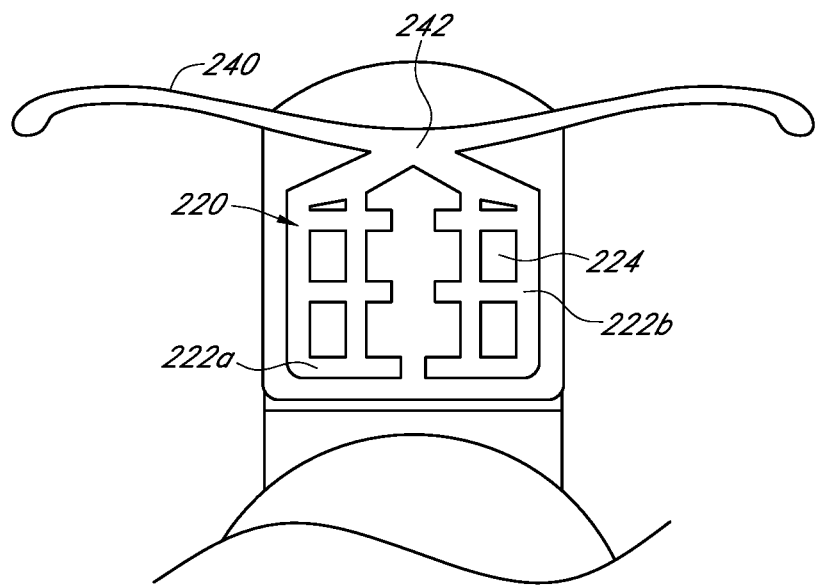
FIG. 5A-5G illustrates top views of exemplary semi-rigid framework for plate haptics according to an embodiment of the present invention.
Figure 5B:
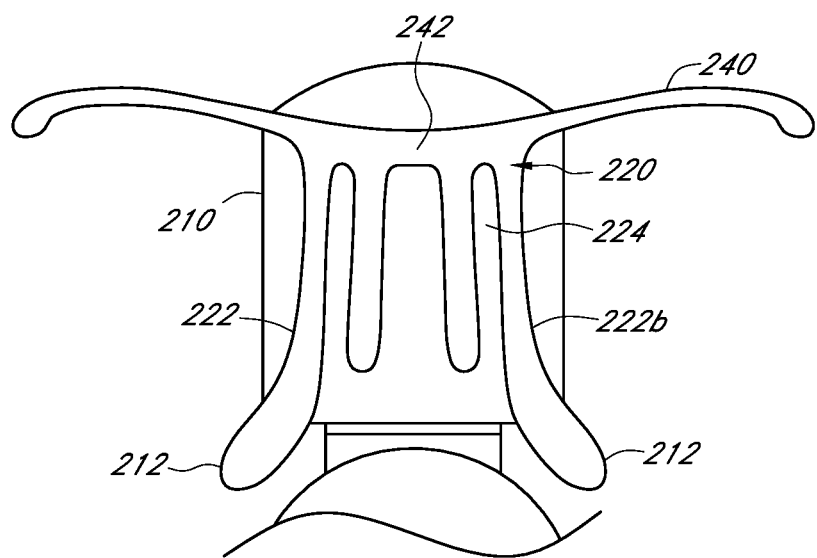

As shown in FIG. 5A, the chassis 220 may principally comprise a plurality of lateral frame members 222a crisscrossing a plurality of longitudinal frame members 222b. Specifically, as shown in FIG. 5A, the frame members 222 may be disposed so as to resemble the letter "E" and it's mirror image about the longitudinal axis of the intraocular lens. Additional frame members 220 may extend diagonally to intersect the centration member 240 at the base 242. As seen in FIG. 5A, the centration member 240 and the chassis 220 may comprise a unitary structure.

As shown in FIG. 5B, the chassis 220 may principally comprise a plurality of longitudinal frame members 222b disposed substantially parallel to each other and symmetrical about the longitudinal axis of the intraocular lens. Specifically, as shown in FIG. 5B, the frame members 222 may be disposed so as to resemble the Greek letter "n". Additional frame members 220 may extend longitudinally downward from the crossing lateral frame member 222a which may form the base 242 of the centration member 240. As seen in FIG. 5B, the centration member 240 and the chassis 220 may comprise a unitary structure. Additionally, as seen in FIG. 5B, the chassis 220 may form the tabs 212 via frame members 222 extending beyond the haptic body 210.

Figure 5C:
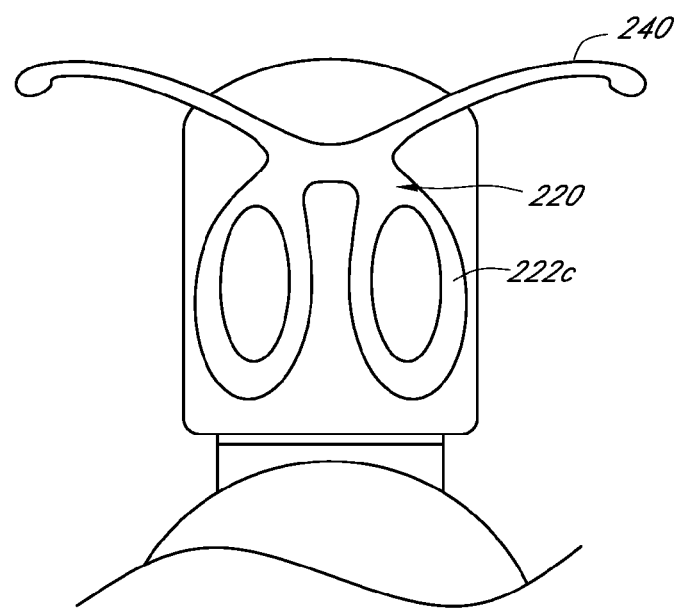
Figure 5D:
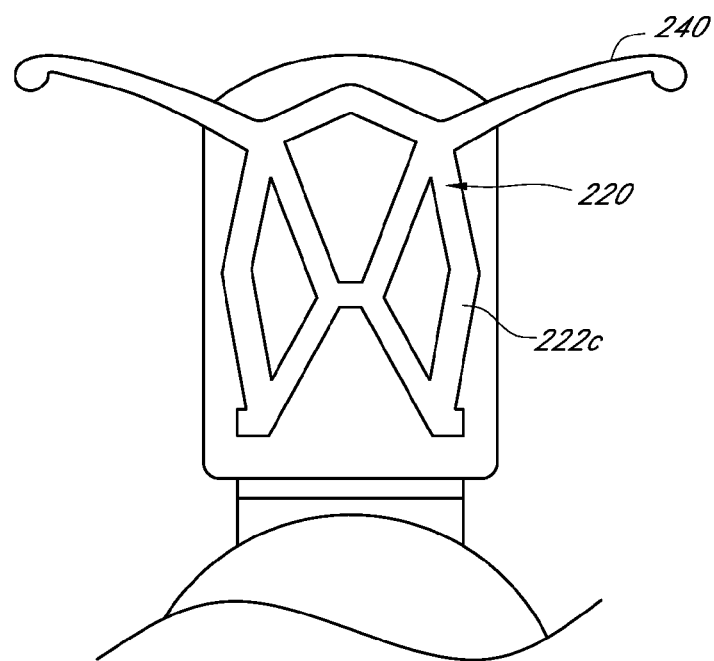

As shown in FIGS. 5C and 5D, the chassis 220 may principally comprise a plurality of elliptical frame members 222c symmetrically spaced from each other about the longitudinal axis of the intraocular lens. Specifically, as shown in FIGS. 5C and 5D, the frame members 222 may be integral to the base 242 of the centration member 240. As seen in FIGS. 5C and 5D, the centration member 240 and the chassis 220 may comprise a unitary structure. Additional frame members 222 may extend to connect the substantially elliptical frame members 222c or to provide further structural support.

Figure 5E:
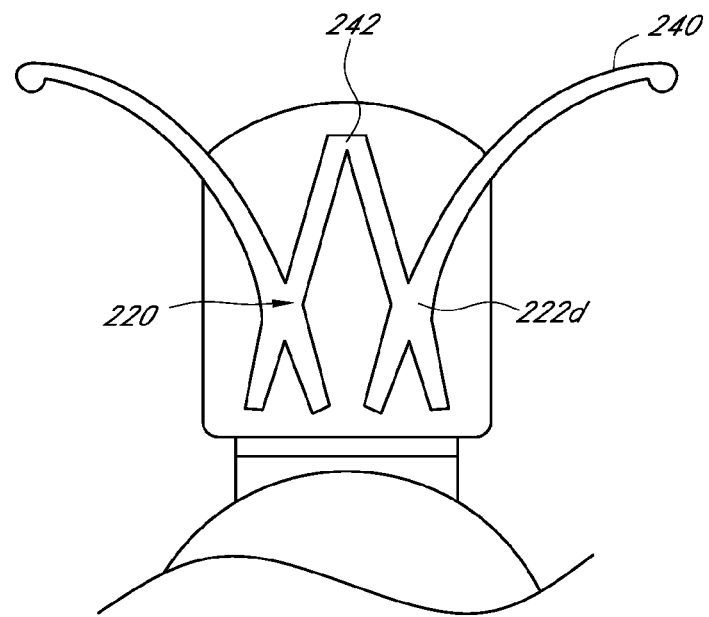

As shown in FIG. 5E, the chassis 220 may principally comprise a plurality of cross-diagonally disposed and intersecting frame members 222d. Specifically, as shown in FIG. 5E, the frame members 222d may be disposed so as to resemble the letter "x" and it's mirror image about the longitudinal axis of the intraocular lens. Additional frame members 220 may extend from the frame members 222d to join them. As shown in FIG. 5E, the intersection of the frame members 222d may form the base 242 of the centration member 240. As seen in FIG. 5E, the centration member 240 and the chassis 220 may comprise a unitary structure.

Figure 5F:
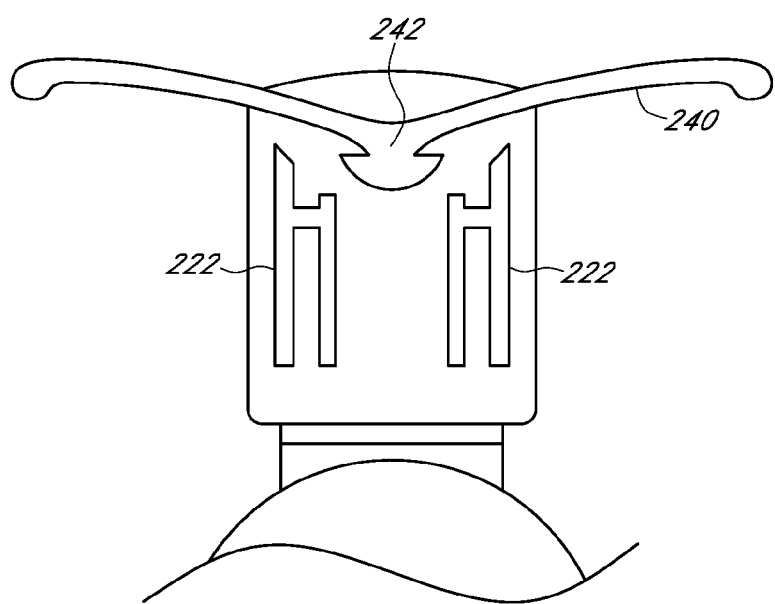
Figure 5G:
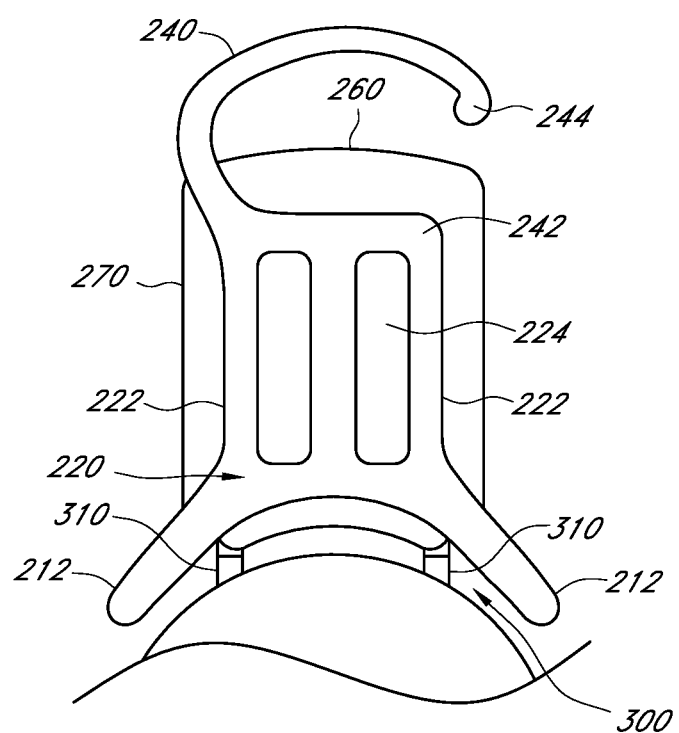
Figure 6:
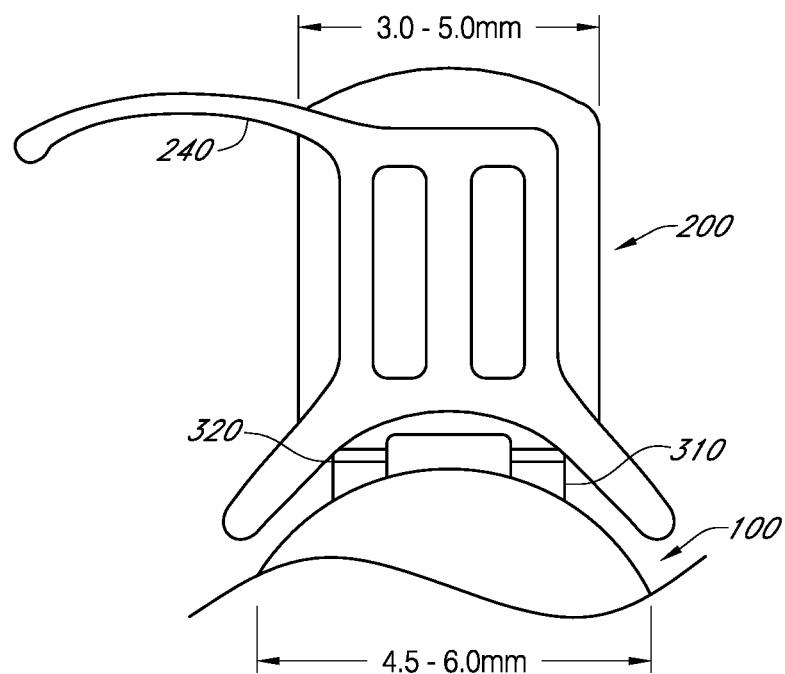
FIG. 6 illustrates a plate haptic accommodating intraocular lens according to an embodiment of the present invention.
Figure 7:
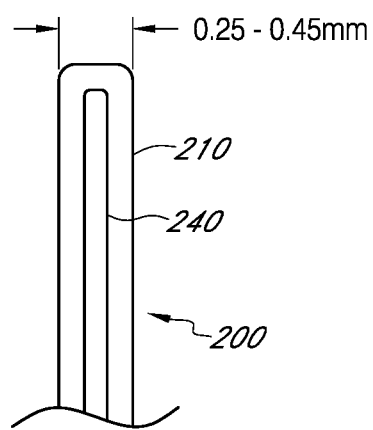
FIG. 7 illustrates a plate haptic accommodating intraocular lens according to an embodiment of the present invention.

As shown in FIG. 5F, the chassis 220 may principally comprise a plurality of longitudinal frame members 222b disposed substantially parallel to each other. Specifically, as shown in FIG. 5F, the frame members 222 may be disposed so as to resemble the letter "h" and it's mirror image about the longitudinal axis of the intraocular lens. As seen in FIG. 5F, the centration member 240 and the chassis 220 may comprise a separate structures. Additionally, as seen in FIG. 3B, the chassis 220 itself may comprise a multi-piece structure, or in other words, the chassis 220 may comprise multiple chassis 220.

As shown in FIG. 5G, the chassis 220 may principally comprise a plurality of longitudinal frame members 222b disposed substantially parallel to each other and intersected at either ends by lateral frame members 222a. Specifically, as shown in FIG. 5G, the frame members 222 may be disposed so that a plurality of frame members 222 are displaced equidistant from the longitudinal axis of the intraocular lens and a single frame member 222 is substantially coincident with the longitudinal axis. Additional frame members 220 may extend longitudinally downward from a crossing lateral frame member 222a which may form the base 242 of the centration member 240. As seen in FIG. 5G, the centration member 240 and the chassis 220 may comprise a unitary structure. Additionally, as seen in FIG. 5G, the chassis 220 may form the tabs 212 via frame members 222 extending beyond the haptic body 210.

Figure 4B:
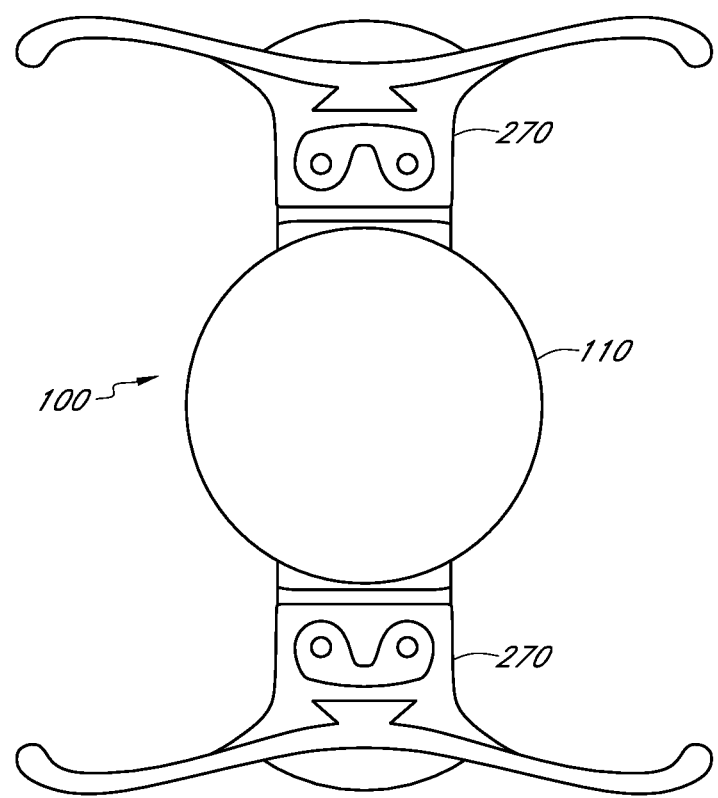
Figure 4C:
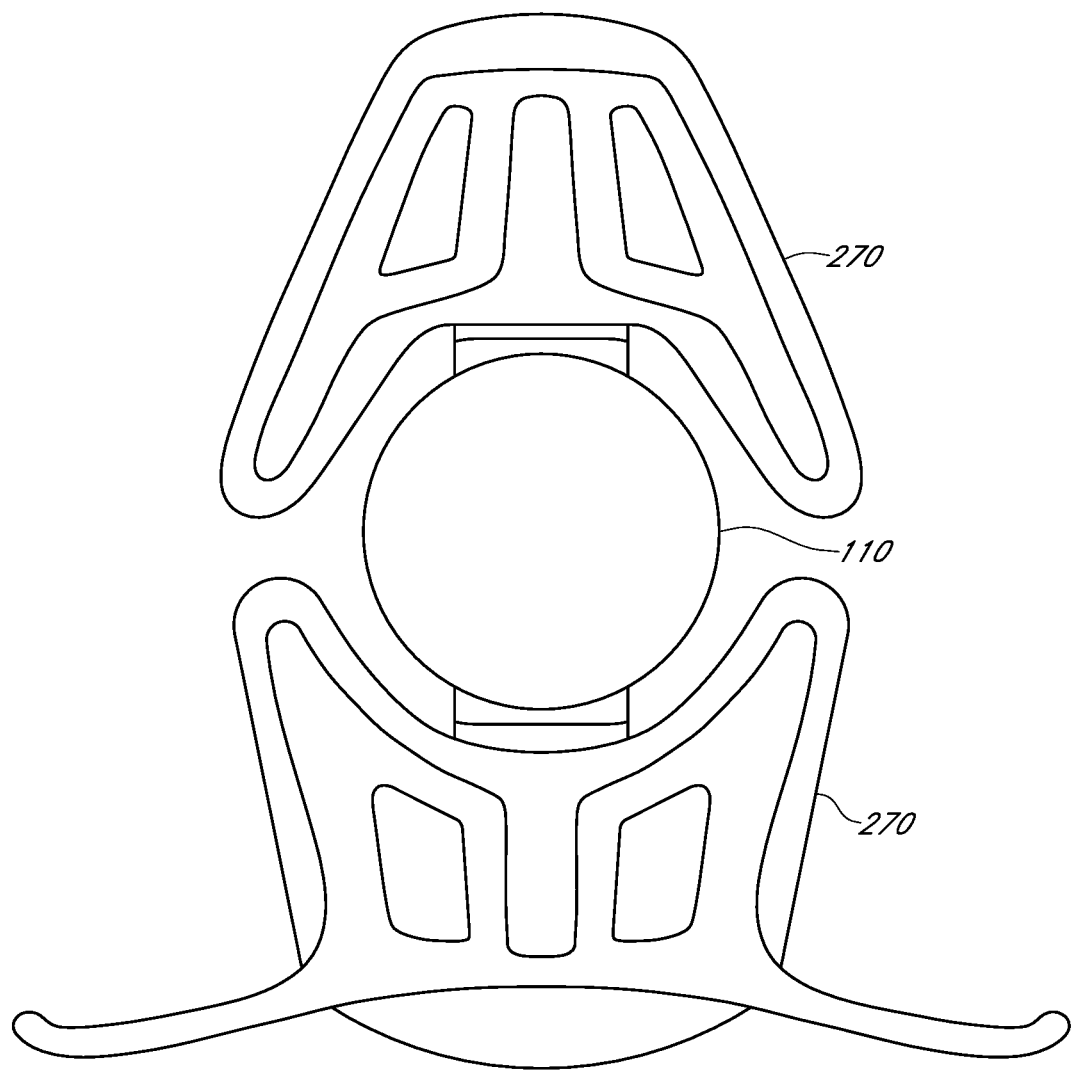

As shown in FIG. 4B, the lens optic 100 may have a periphery 110 that extends laterally beyond the lateral sides 250 of the plate haptic 200. However, as shown in FIG. 4C, the lateral sides may extend laterally beyond the periphery 110, and as shown in FIG. 4B, the lateral sides 250 may be tangential to the periphery 110. The lens optic 100 may be made of a flexible optical material such as silicone, acrylic, hydrogels, or other similar material, and is substantially flexible so as to enable folding and insertion into an eye. Furthermore, the lens optic 100 is preferably shaped so as to be biconvex, refractive, diffractive, plano-convex, Fresnel, spheric, aspheric, toric or multifocal.

In application, the accommodating intraocular lens is folded laterally so as to enable insertion through a small incision into the eye. The substantially flexible nature of the plate haptic 200 permits this folding. Once in the eye, the accommodating intraocular lens unfolds and is secured within the capsular bag. During accommodation the ciliary muscle exerts radial pressure on the ends of the haptics 200, moving them centrally and posteriorly towards the optic 100. Because it is substantially longitudinally rigid, the plate haptic 200 resists bending to the radial force exerted by the ciliary muscle. However, the stretchable hinge portion 300 is less resistant to the pressure from the vitreous cavity, and therefore stretches and flexes on application of the pressure. The separation of straps 310 ensures the transferred pressure is uniform, while the addition of the grooves 320 further weakens the straps 310 resistance to flexion/stretching. Thus, with the increase in vitreous cavity pressure, the optic 100 is pushed forward along the axis of the eye, the optic 100 moving forward relative to both the proximal 250 and distal portions 260 of the plate haptics 200, resulting in superior accommodation.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for anyone of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that the named inventor believes that the claimed subject matter is what is intended to be patented.

What is claimed is:

1. An intraocular lens comprising:
   an optic configured to be vaulted posteriorly in the eye after insertion; and
   at least one plate haptic comprising:
   a haptic body substantially rigid in a longitudinal direction and having a proximal end relative to said optic and a distal end which haptic comprises a rigid structure embedded in a flexible material and said haptic having a fixed length, wherein the intraocular lens has a uniplanar configuration prior to insertion in an eye and is adapted to transition to a posterior vaulted configuration when implanted wherein the rigid structure has the same length in each configuration and wherein said at least one haptic is capable of resisting bending pressure exerted on its distal end by the ciliary muscle and fibrosis to leave the optic in the same position along an axis.

2. The intraocular lens of claim 1, wherein said rigid structure is a chassis,
   said chassis being integral to the haptic body.

3. The intraocular lens of claim 2, further comprising:
   at least one centration member extending substantially laterally from and integral to a distal portion of the haptic body, the centration member operable to engage a capsular bag.

4. The intraocular lens of claim 3, wherein the at least one centration member is integral to the chassis.

5. The intraocular lens of claim 2, further comprising:
   a plurality of laterally divergent paddles extending from and integral to opposing ends of a proximal portion of the haptic body; and
   wherein when the haptic body is coupled to the optic, and the paddles partially surround the optic.

6. The intraocular lens of claim 5, wherein the paddles are integral with the haptic body and the chassis integral thereto.

7. The intraocular lens of claim 5, wherein the paddles comprise the chassis extending from the plate haptic body.

8. The intraocular lens of claim 2, wherein the chassis is a unitary structure.

9. The intraocular lens of claim 2, wherein the chassis is multi-piece structure.

10. The intraocular lens of claim 2, wherein the chassis is symmetric about a longitudinal axis of the haptic body.

11. The intraocular lens of claim 2, wherein the haptic body is made of a first material, and the chassis is also made of the first material.

12. The intraocular lens of claim 2, wherein the haptic body is made of a first material, and the chassis is made of a second material different from the first material.

13. The intraocular lens of claim 12, wherein the second material is at least one of: polyimide, prolene, PMMA, and titanium.

14. The intraocular lens of claim 2, wherein the haptic body has a thickness of 0.2 mm to 0.45 mm.

15. The intraocular lens of claim 1, wherein said lens is capable of providing uncorrected vision at all distances by depth of focus.

16. An intraocular lens comprising:
   a flexible optic configured to be vaulted posteriorly in the eye after insertion; and
   a pair of plate haptics connected to the optic, each haptic comprising a proximal end and a distal end, the proximal end being closer to the optic than the distal end, each haptic comprising a single and separate rigid chassis structure at least partially embedded in a flexible material and having a fixed length;

wherein each rigid chassis structure comprises:
a plurality of elongate members extending in a longitudinal direction and a transverse member connecting the elongate members, and
wherein each of said haptics comprises a pair of laterally and longitudinally extending paddles which partially surround said optic with said chassis structure extending into said paddles,
wherein the intraocular lens has a uniplanar configuration and a posterior vaulted configuration, the intraocular lens being configured to transition from the uniplanar configuration to the posterior vaulted configuration after implantation;
wherein the length of each of the rigid structures is fixed and is the same in the uniplanar configuration and the posterior vaulted configuration; and
wherein the pair of haptics are capable of resisting bending from pressure exerted on the distal ends of the haptics by contraction of the ciliary muscle and fibrosis to generally leave the optic in the same position along an optical axis of the eye when the intraocular lens is positioned in the capsular bag, wherein the lens is capable of providing uncorrected vision at all distances by the depth of focus.

17. The intraocular lens of claim 16, wherein each haptic is foldable about a longitudinal axis of the haptic.

18. The intraocular lens of claim 16, wherein a longitudinal dimension of the intraocular lens is between about 9.5 mm and about 12.0 mm.

19. The intraocular lens of claim 16, wherein the rigid structure is connected to the flexible optic by a short extension of the flexible optic.

20. The intraocular lens of claim 16, wherein the flexible material and the optic comprise the same material.

21. The intraocular lens of claim 16, wherein the flexible material comprises silicone or acrylic.

22. The intraocular lens of claim 16, wherein said at least one loop is a closed loop.

23. The intraocular lens of claim 16, wherein said at least one loop is an open loop.

24. The intraocular lens of claim 16, wherein the loop structure had a width that is less than the width of one of the plate portions.

25. The intraocular lens of claim 16, wherein the rigid structure comprises extensions at a distal end thereof.

26. The intraocular lens of claim 16, wherein said at least one transverse bar is disposed at a distal end of its respective rigid structure.

27. The intraocular lens of claim 16, wherein at least one haptic is connected to the flexible optic by a short extension.

28. The intraocular lens of claim 16, wherein said lens is non-accommodating.

29. The intraocular lens of claim 16, wherein at least one haptic is connected to the flexible optic by a torsion bar.

30. The intraocular lens of claim 16, wherein at least one haptic is connected to the flexible optic by a hinge.

31. An intraocular lens comprising:
a flexible optic configured to be vaulted posteriorly in the eye after insertion into the eye; and
a pair of haptics connected to the optic, each haptic comprising a proximal end and a distal end, the proximal end being closer to the optic than the distal end, each haptic comprising:
at least two rigid paddles contiguous with and extending laterally from each haptic, and
a rigid structure at least partially embedded in a flexible material, said rigid structure having elements extending longitudinally in said flexible material;
wherein the intraocular lens comprises a uniplanar configuration and a posterior vaulted configuration, the intraocular lens being configured to transition from the uniplanar configuration to the posterior vaulted configuration after implantation;
wherein the length of each rigid structure is fixed and is the same in the uniplanar configuration and the posterior vaulted configuration; and
wherein the pair of plate haptics are resistant to bending from pressure exerted on the distal ends of the haptics by contraction of the ciliary muscle and fibrosis to generally leave the optic consistently in the same position along an optical axis of the eye when the intraocular lens is positioned in the capsular bag and is capable of providing uncorrected vision at all distances by depth of focus.

32. The intraocular lens of claim 31, wherein said haptic is foldable about a longitudinal axis of the haptic.

33. The intraocular lens of claim 31, wherein said loops are closed loops.

34. The intraocular lens of claim 31, wherein said loops are open loops.

35. The intraocular lens of claim 31, wherein the haptic paddles and the optic comprise the same material.

36. The intraocular lens of claim 31, wherein the flexible material comprises silicone or acrylic.

37. The intraocular lens of claim 31, wherein said lens is non-accommodating.

38. An intraocular lens comprising:
a flexible optic configured to be vaulted posteriorly in the eye after insertion in the eye; and
a pair of haptics connected to the optic, each haptic comprising a proximal end and a distal end, the proximal end being closer to the optic than the distal end, each haptic comprising a rigid structure having laterally extending paddles and a plurality of loops;
wherein the intraocular lens comprises a uniplanar configuration and a posterior vaulted configuration, the intraocular lens being configured to transition from the uniplanar configuration to the posterior vaulted configuration after implantation;
wherein each rigid structure has a fixed length in the uniplanar configuration and the posterior vaulted configuration; and
wherein the pair of haptics are resistant to bending from pressure exerted on the distal ends of the haptics by contraction of the ciliary muscle and fibrosis to generally leave the optic in the same position along an optical axis of the eye when the intraocular lens is positioned in the capsular bag.

39. The intraocular lens of claim 38, wherein each haptic is foldable about a longitudinal axis of the haptic.

40. The intraocular lens of claim 38, wherein said loops are closed loops.

41. The intraocular lens of claim 38, wherein said loops are open loops.

42. The intraocular lens of claim 38, wherein said intraocular lens is monolithic.

43. The intraocular lens of claim 38, wherein the flexible optic and each haptic comprise the same material.

44. The intraocular lens of claim 43, wherein the same material is acrylic.

45. The intraocular lens of claim 38, wherein said lens is non-accommodating.

* * * * *